United States Patent [19]

Aoki et al.

[11] 4,228,098

[45] Oct. 14, 1980

[54] PROCESS FOR THE PREPARATION OF ACRYLONITRILE

[75] Inventors: Kunitoshi Aoki; Makoto Honda, both of Tokyo; Tetsuro Dozono, Yokosuka; Tsutomu Katsumata, Yokohama, all of Japan

[73] Assignee: Asahi Kasei Kogyo Kabushiki Kaisha, Osaka, Japan

[21] Appl. No.: 971,293

[22] Filed: Dec. 20, 1978

[30] Foreign Application Priority Data

Dec. 31, 1977 [JP] Japan ................................ 52-159797

[51] Int. Cl.$^2$ ........................................... C07C 120/14
[52] U.S. Cl. ................................................. 260/465.3
[58] Field of Search ..................................... 260/465.3

[56] References Cited

U.S. PATENT DOCUMENTS

| | | | |
|---|---|---|---|
| 2,904,580 | 9/1959 | Idol, Jr. ............................ | 260/465.3 |
| 3,135,783 | 6/1964 | Sennewald et al. ............... | 260/465.3 |
| 3,629,148 | 12/1971 | Dominik et al. ............... | 260/465.3 X |
| 3,642,930 | 2/1972 | Grasselli et al. ............... | 260/465.3 X |
| 3,712,912 | 1/1973 | Hausweiler et al. ............. | 260/465.3 |
| 3,766,092 | 10/1973 | Honda et al. .................. | 260/465.3 X |
| 3,907,859 | 9/1975 | Grasselli et al. ................ | 260/465.3 |
| 3,993,680 | 11/1976 | Grasselli et al. ................ | 260/465.3 |
| 4,123,453 | 10/1978 | Grasselli et al. ................ | 260/465.3 |

FOREIGN PATENT DOCUMENTS

| | | |
|---|---|---|
| 1243175 | 6/1967 | Fed. Rep. of Germany . |
| 2104223 | 8/1972 | Fed. Rep. of Germany . |
| 38-17967 | 9/1963 | Japan . |
| 46-5068 | 1/1971 | Japan . |
| 47-39025 | 6/1972 | Japan ................................ 260/465.3 |
| 47-16419 | 9/1972 | Japan . |
| 48-13290 | 2/1973 | Japan . |
| 50-129519 | 10/1975 | Japan . |
| 51-28617 | 8/1976 | Japan . |
| 1347175 | 2/1974 | United Kingdom . |

OTHER PUBLICATIONS

Kunii et al., Fluidization Engineering, 1962, pp. 8–11, John Wiley & Sons, Inc., N.Y.

*Primary Examiner*—Joseph Paul Brust
*Attorney, Agent, or Firm*—Sprung, Felfe, Horn, Lynch & Kramer

[57] ABSTRACT

A process for the preparation of acrylonitrile by the ammoxidation reaction of propylene, characterized by using an oxide type catalyst which contains, as active ingredients, molybdenum, bismuth, iron and at least one element selected from potassium, rubidium and cesium in specifically limited proportions and which may further contain sodium and/or phosphorus. By the use of such a specific catalyst, the selectivity for the desired acrylonitrile is remarkably improved, and there can be attained high yield of the product. In the process of the present invention, the catalyst can maintain a high activity and a high selectivity for a long time, without undergoing attrition. The catalyst is well prevented from sublimation-escaping of the ingredient molybdenum therefrom.

8 Claims, 1 Drawing Figure

FIGURE
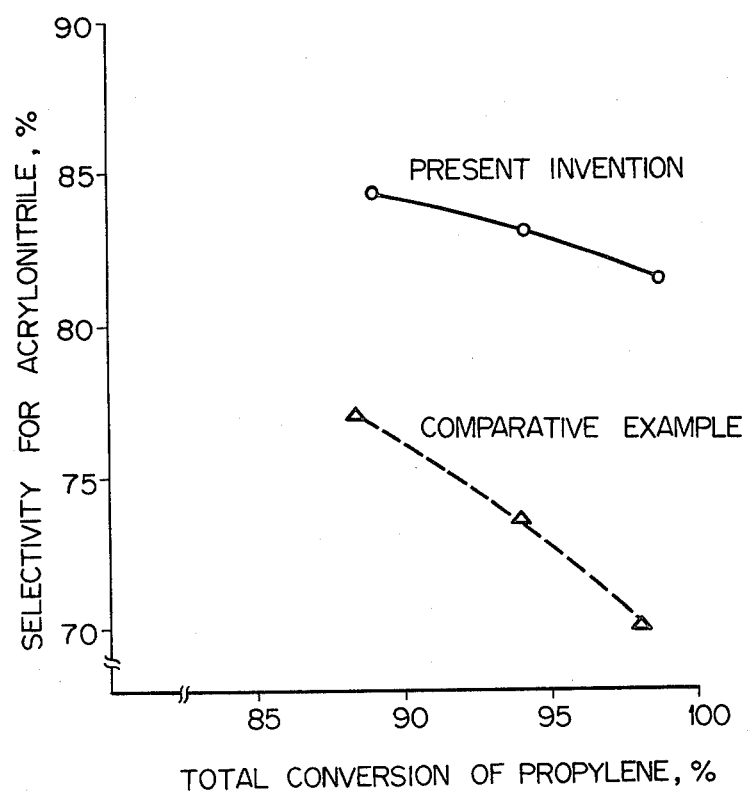

PROCESS FOR THE PREPARATION OF ACRYLONITRILE

This invention relates to a process for the preparation of acrylonitrile by the ammoxidation of propylene. More particularly, the present invention is concerned with a process for the preparation of acrylonitrile by the gaseous phase reaction of propylene with ammonia and oxygen in the presence of an improved multi-active ingredient type catalyst containing oxides of molybdenum, bismuth, iron and other specific elements in specific proportions.

The process of producing acrylonitrile by the gaseous phase oxidation of propylene with molecular oxygen in the presence of ammonia is well-known as the "ammoxidation of propylene", and widely practiced on an industrial scale. As the catalysts to be used in the ammoxidation reaction of propylene, there have been proposed many kinds of catalysts. Among them, however, only limited kinds of catalysts are practically used. One of the noticeable catalysts is disclosed in German Pat. No. 1,243,175, and it is an oxide type catalyst comprising the oxides of molybdenum, bismuth, iron and phosphorus. This oxide type catalyst is an improvement of the oxide type catalyst comprising the oxides of molybdenum, bismuth and phosphorus which is disclosed in U.S. Pat. No. 2,904,580, said improvement residing in that iron is additionally incorporated whereby the activity of the catalyst is increased.

Various improvements have been proposed with respect to the above-mentioned oxide type catalyst (see, for example, U.S. Pat. No. 3,629,148, Japanese patent application laid-open specification No. 5068/1971, German application laid-open specification No. 2,104,223, Japanese patent application laid-open specification No. 13290/1973 and Japanese patent application publication No. 28617/1976). These proposed catalysts, however, still have disadvantages, particularly in that the side reactions cannot be sufficiently suppressed and hence the selectivity of the reaction for acrylonitrile is relatively low.

The inventors of the present invention have already proposed an oxide type catalyst for the ammoxidation of propylene which contains sodium, as one of the requisite active ingredients, in addition to molybdenum, bismuth, iron and phosphorus (see Japanese patent application laid-open specification No. 129519/1975), but the proposed catalyst is still insufficient in yield of the desired acrylonitrile for practical use of the catalyst on an industrial scale.

With a view to developing an excellent catalyst for the production of acrylonitrile by the ammoxidation of propylene, the present inventors have made intensive studies on the chemical and physical structures and catalysis of a Mo-Bi-Fe oxide type catalyst system. As a result, they have found that when the respective proportions of molybdenum, bismuth and iron in the catalyst composition are specified within the extremely narrow ranges and a minute amount of at least one element selected from potassium, rubidium and cesium is additionally incorporated into the catalyst system as a further requisite active ingredient, the activity and the selectivity of the catalyst are remarkably improved; that when the relative amount of molybdenum to the catalyst composition is comparatively reduced, the sublimation-escaping of the molybdenum from the catalyst composition is effectively suppressed; that the further incorporation of sodium into the catalyst system is effective for the suppression of sublimation-escaping of the molybdenum from the catalyst, especially when the molybdenum content of the catalyst is relatively large; and that when silica is used as the support material for the active ingredients, a high attrition resistance is imparted to the catalyst, and the attrition resistance of the catalyst can be further improved by the incorporation of a small amount of phosphorus into the catalyst system. Based upon such novel findings, the present invention has been made.

Accordingly, it is an object of the present invention to provide a process for the preparation of acrylonitrile by the ammoxidation of propylene in the presence of a catalyst, which can produce the desired acrylonitrile in high yield.

It is another object of the present invention to provide a process of the kind described above, in which, by the use of a specific catalyst composition, the escaping of the active ingredient from the catalyst can be effectively prevented whereby the ammoxidation reaction can be carried out stably.

It is a further object of the present invention to provide a process of the character described, which can be carried out without attrition of the catalyst and can be continuously effected in a fluidized bed reaction system for a prolonged period of time.

The foregoing and other objects, features and advantages of the present invention will be apparent to those skilled in the art from the following detailed description taken in connection with the accompanying drawing in which:

FIGURE is a graph showing the relationship between the selectivity for acrylonitrile and the total conversion of propylene, with respect to the catalyst to be used in the process of the present invention, shown in comparison with that of the catalyst falling outside the scope of the present invention.

According to the present invention, there is provided a process for the preparation of acrylonitrile by the gaseous phase reaction of propylene with ammonia and molecular oxygen in the presence of a catalyst, characterized in that the catalyst comprises:

a catalyst composition represented by the following general formula $$A_aMoBi_bFe_fNa_nP_pO_q$$

wherein

A is at least one element selected from potassium, rubidium and cesium;

a, b, f, n, p and q are numbers respectively representing atomic ratios of A, bismuth, iron, sodium, phosphorus and oxygen relative to one atom of molybdenum, provided that;

a is a number of 0.002 to 0.02;

p is a number of 0 to 0.2;

q is the number of oxygens required to satisfy the valence requirements of the other elements present; and b, f and n are numbers respectively defined by the following formulae $$b = \frac{(1-X)(1-Y)(1-Z)}{Y} + \frac{1}{2}Z + p,$$

$$f = \frac{X(1-Y)(1-Z)}{Y} \text{ and } n = \frac{1}{2}Z$$

wherein

X and Y are respectively numbers falling within the area defined by a quadrilateral formed by lines connecting points (0.45, 0.35), (0.45, 0.65), (0.85, 0.50) and (0.85, 0.65) on an XY diagrammatic system of coordinates; and Z is a number of 0 to 0.6;

said catalyst composition being supported on 30 to 70% by weight, based on said catalyst, of silica.

In the process of the present invention, in order that the catalyst to be used has effective functions and properties, it should have an extremely limited composition of active ingredients. Particularly, the catalyst is characterized by having a minute amount of an ingredient A incorporated thereinto. In the acrylonitrile production using the conventional catalyst in which there is incorporated no ingredient A, as is apparent from FIGURE in the accompanying drawing, not only the selectivity for acrylonitrile is low, but also as the conversion of propylene is increased by prolonging the contact time a part of the acrylonitrile produced is adversely caused to undergo the secondary decomposition which leads to large lowering of selectivity.

In the process of the present invention in which a catalyst having an ingredient A incorporated therein is used, a high selectivity for acrylonitrile is obtained even at a total conversion of propylene as high as substantially 100%. In the catalyst to be used in the process of the present invention, the amount of the ingredient A is within the range of the index a defined by the aforementioned catalyst composition formula in which $a = 0.002$ to 0.02, preferably 0.004 to 0.012. The ingredient A is selected from potassium, rubidium and cesium. They may be employed alone or in combination. In general, from the viewpoint of economics as well as yield of the desired acrylonitrile, potassium is advantageously employed. Where the amount of the ingredient A in the catalyst to be used in the process of the present invention exceeds the range defined above, not only the rate of conversion of propylene is low but also the ammonia becomes less reactive, disadvantageously leading to increase in byproduction of acrolein.

In the catalyst composition in the catalyst to be used in the process of the present invention, the values of the index X and the index Y are expressed by a point falling within the area defined by a quadrilateral formed by lines connecting points (0.45, 0.35), (0.45, 0.65), (0.85, 0.50) and (0.85, 0.65) on an XY diagrammatic system of coordinates. Where the values of the indices X and Y are outside the above-defined area, there cannot be realized a high selectivity for acrylonitrile even if the catalyst has an ingredient A incorporated therein. Especially when the value of the index Y exceeds the range defined by the above-mentioned area, in the production of acrylonitrile by the use of such a catalyst, the selectivity for acrylonitrile is lowered and, at the same time, the escaping of molybdenum from the catalyst becomes large, leading to troubles such as clogging of the reactor at its outlet portion.

The amount of sodium can be defined by using the index Z through the formula $n = \frac{1}{2}Z$. The value of the index Z is in the range of 0 to 0.6, preferably 0 to 0.45.

As stated before, the inventors of the present invention already developed a Mo-Bi-Fe-P oxide type catalyst in which sodium is additionally incorporated as a further requisite active ingredient as disclosed in Japanese patent application laid-open specification No. 129519/1975. As a result of further investigations, it has been found that insofar as the values of the indices X and Y fall within the above-defined area and there is incorporated a defined minute amount of the ingredient A, there can be obtained a catalyst which is excellent in selectivity for acrylonitrile as well as in activity even if there is incorporated no sodium, i.e., $Z = O$. Where no sodium is incorporated in a catalyst to be used in the process of the present invention, it is preferred, from a viewpoint of the prevention of escaping of molybdenum from the catalyst, that the values of the indices X and Y fall within the area defined by a quadrilateral formed by the lines connecting points (0.45, 0.35), (0.45, 0.55), (0.85, 0.50) and (0.85, 0.55) on an X-Y diagram.

Where the value of the index Y falls within the area defined with respect to the present invention but is as relatively large as 0.65 to more than 0.55, the escaping of molybdenum from the catalyst tends to be relatively large. In such a catalyst system having a relatively large value of the index Y, however, the escaping of molybdenum from the catalyst can be effectively prevented by incorporation of sodium into the catalyst system. On the other hand, where the value of the index Y is as relatively small as 0.55 or less, the sublimation-escaping of molybdenum from the catalyst can be well prevented even without incorporation of sodium into the catalyst system and can be industrially used without any trouble. In order to use the catalyst in the ammoxidation reaction system for a prolonged period of time, it is necessary to prevent escaping of the molybdenum from the catalyst. For this purpose, the above-defined range with respect to the index Z is sufficient. If the value of the index Z exceeds the defined range, the yield of the desired acrylonitrile is lowered.

In the catalyst to be used in the process of the present invention, silica is employed as a support material for the catalyst composition containing active ingredients. Silica is in itself inert as compared with other support materials, and can serve as an excellent binder for the active ingredients without impairing the selectivity of the catalyst composition and serve to impart to the resulting catalyst a high attrition resistance. If other material, e.g. titania or zirconia is used as a support material for the present catalyst composition, it can hardly exert a binding effect. Further, if alumina is employed as the support material, it can serve as a binder but unfavorably causes the selectivity of the catalyst to be lowered. In this connection, it should be noted that if alumina is contained in the present catalyst system even only in an amount as small as 1% by weight, the selectivity is lowered. The amount of silica to be used may be in the range of 30 to 70% by weight, preferably 40 to 60% by weight, based on the total weight of the catalyst. If the amount of silica is less than 30% by weight, there cannot be obtained a sufficient attrition resistance. On the other hand, if the amount of silica exceeds 70% by weight, the concentration of catalyst composition of the active ingredients in the catalyst is lowered and, as a result, not only a sufficient activity of the catalyst cannot be obtained but the selectivity is also lowered drastically.

The amount of phosphorus in the catalyst composition of active ingredients is defined by the index p. The value of the index p is in the range of 0 to 0.2, preferably 0.05 to 0.15. In the catalyst to be used in the process of the present invention, an attrition resistance of the catalyst can be further improved by incorporation of a minute amount of phosphorus. In this connection, it is noted that in preparing a slurry of raw materials for the production of a catalyst (of which explanation will be given later), the phosphorus incorporated functions to make the size of the suspensoid in the slurry fine and to improve dispersibility of the suspensoid in the slurry. It is believed that, according to such functions of the phosphorus, a silica sol employed as the source of the support silica and the active ingredients of the catalyst composition can be brought into a homogeneously mixed state in the slurry, leading to an excellent attrition resistance of the catalyst in the finished form. Phosphorus can be employed in an amount exceeding the range defined in the present invention, but the use of the excessive amount of phosphorus does not lead to increase of attrition resistance.

The catalyst composition defined by the aforementioned formula is present, in the catalyst, in an amount of substantially 30 to 70% by weight, preferably 40 to 60% by weight based on the weight of the catalyst.

In general, when a catalyst is used on a commercial scale, it must be durable, with respect to its functions, under the reaction conditions for a long period of time. In this respect, as stated above, the catalyst to be used in the process of the present invention has not only improved activity and selectivity in the initial stage of the reaction, but also can maintain high activity and selectivity for a long period of time because of high stability of the active ingredients in the catalyst as well as high attrition resistance of the finished catalyst itself.

The process of the present invention may be conducted either in a fluidized bed reactor or a fixed bed reactor. When a fluidized bed reactor is employed for the practice of the present invention, removal of the reaction heat can be easily effected so that the temperature distribution in the reactor may be uniform, and therefore the practice of the present invention in a fluidized bed reactor is suitable for the production of acrylonitrile on a large scale. In general, when a catalyst is used in a fluidized bed reactor, the particles of the catalyst come into collision with each other and with the inner wall of the reactor and are caused to be attrited. The catalyst to be used in the process of the present invention has a sufficient attrition resistance so that it is durable for a long period of time.

The catalyst to be used in the process of the present invention may be prepared by a method comprising the steps of (1) preparing a slurry of raw materials, (2) spray-drying the resulting slurry and (3) heat-treating the resulting spray-dried product for calcination thereof. The preparation method of the catalyst may be practiced in the similar manner to that described in Japanese patent application laid-open specification No. 129519/1975.

As the source of a support silica, a silica sol may be suitably employed. As the source of phosphorus, there may preferably be employed phosphoric acid. As the sources of molybdenum, bismuth, iron, sodium, potassium, rubidium and cesium, there may advantageously be employed their respective salts soluble in water or nitric acid, for example, ammonium salts, nitrates, chlorides, sulfates and salts of organic acids such as oxalic acid, acetic acid and the like. Particularly, in respect of the source of molybdenum, it is preferable to employ an ammonium salt of molybdenum, and in respect of the sources of bismuth, iron, sodium, potassium, rubidium and cesium, there are preferably employed nitrates thereof.

In the step (1), as mentioned above, a slurry of raw materials is prepared. Illustratively stated, first, phosphoric acid is added to a silica sol while stirring (in case the incorporation of phosphorus is intended). Secondly, an aqueous solution of ammonium paramolybdate is added and lastly, there is added a solution of a mixture of bismuth nitrate, ferric nitrate, sodium nitrate (in case the incorporation of sodium is intended) and at least one member selected from potassium nitrate, rubidium nitrate and cesium nitrate in diluted nitric acid. Thus, there is obtained a slurry in which the fine particles of suspensoids are uniformly dispersed in the silica colloid sol. In the above procedures, when phosphoric acid is employed, there can be obtained a slurry having excellent uniformity.

In the step (2), the slurry thus obtained is spray-dried using an ordinary spray-drying apparatus to obtain dried spherical particles. The spraying of the slurry may be conducted by any type of methods usually employed in industries, e.g., a centrifugal type, a two-fluid nozzle type or a high pressure nozzle type spraying method, but the centrifugal type spraying method is particularly preferred. In the centrifugal type spraying method, the diameters of the product catalyst particles can be adjusted by regulating the rotation speed of the disc and the rate of supply of the slurry so that the diameters of the catalyst particles may be distributed within the range suitable for use in a fluidized bed reactor, that is, within the range of 10 to 150 microns.

In the step (3), the spray-dried product obtained in the step (2) is subjected to heat-treatment for calcination, using an ordinarily employed kiln, such as a tunnel type or a rotary type kiln. The calcination temperature may be 600° to 750° C., preferably 620° to 710° C. The calcination time varies depending on the calcination temperature but is usually 1 to 20 hours.

Propylene and ammonia to be employed in the ammoxidation process of the present invention is not necessarily of so high purity but may be of a grade for the industrial use. As the source of oxygen, there is usually employed air. The volume ratio (propylene:ammonia:air) may be 1:0.9 to 1.5:8 to 11, preferably 1:1 to 1.3:9 to 10. The reaction temperature may be 400° to 500° C., preferably 440° to 480° C. The reaction pressure may be in the range of from reduced pressure to super-atmospheric pressure, and the reaction may usually be conducted under an atmospheric pressure to a pressure of about 2 kg/cm$^2$-gauge. The time of contact of mixed raw gaseous materials with the catalyst may be 0.5 to 15 seconds, preferably 2 to 10 seconds.

As described, according to the present invention, in the ammoxidation reaction of propylene for the preparation of acrylonitrile, the selectivity of the reaction for acrylonitrile is remarkably improved by the use of a specific catalyst having an extremely limited composition of specific ingredients. Furthermore, it should be noted that in the process of the present invention the catalyst can maintain a high activity and selectivity stably for a long period of time without undergoing attrition, so that the desired acrylonitrile can be produced in remarkably improved yield.

The present invention will be illustrated by the following examples, which should not be construed to be limiting the scope of the present invention.

EXAMPLES AND COMPARATIVE EXAMPLES

(1) Preparation of Catalysts

A catalyst composed of oxides supported on 50% by weight, based on the total of the oxides and silica, of silica and having a composition, in terms of active ingredients, of the formula $MoBi_{0.825}Fe_{0.675}K_{0.006}Na_{0.05}P_{0.1}$, which corresponds to a catalyst composition formula having composition indices [X=0.5, Y=0.4, Z=0.1, a(K)=0.006 and p=0.1], was prepared according to the following procedures.

28.8 g of an 85% by weight aqueous solution of phosphoric acid were added to 5,000 g of "Snowtex"-N (trade name of a silica sol manufactured by Nissan Kagaku Kabushiki Kaisha, Japan; "Snowtex" is a registered trade mark) containing 30% by weight of $SiO_2$, while stirring the same, followed by addition of an aqueous solution of 444 g of ammonium heptamolybdate tetrahydrate [$(NH_4)_6Mo_7O_{24}.4H_2O$] dissolved in 1,100 g of water. To the resulting mixture was added a solution composed of 1,010 g of bismuth nitrate pentahydrate [$Bi(NO_3)_3.5H_2O$], 696 g of ferric nitrate nonahydrate [$Fe(NO_3)_3.9H_2O$], 10.6 g of sodium nitrate [$NaNO_3$] and 1.52 g of potassium nitrate [$KNO_3$] dissolved in 1,000 g of a 15% by weight aqueous solution of nitric acid to obtain a slurry. Subsequently, the raw material slurry thus obtained was dried at about 200° C. by means of a parallel flow type spray drier. The raw material slurry was atomized by means of a centrifugal type spraying apparatus equipped with a dish type rotor and disposed in the center of the upper part of the spray drier. The dried powder thus obtained was transferred to a tunnel type calcining kiln in which the powder was calcined at 690° C. for 2 hours to obtain a catalyst. The catalyst thus obtained will be referred to as "Catalyst 1" hereinafter.

According to substantially the same procedures as described above, 40 kinds of catalysts having varied compositions were prepared.

The ammoxidation reactions of propylene were carried out using these catalysts. These catalysts were tested with respect to escaping of molybdenum and attrition of catalyst.

(2) Ammoxidation Reaction of Propylene

(A) Fluidized Bed Process 1,400 g of a catalyst were put into a 3 inches-diameter stainless fluidized bed reactor having therein a 16-mesh stainless net trays. A mixed gas of propylene—ammonia—air (1:1.2:9.0 by volume) was passed through the reactor at a rate of 420 liters/hour in terms of volume under normal temperature and pressure (N.T.P.) conditions while maintaining the reaction temperature at 460° C. and the reaction pressure at 0.5 Kg/cm²-gauge. Under the reaction conditions, the time of contact of the mixed gas with the catalyst was 6.6 seconds.

(B) Fixed Bed Process 2 g of a catalyst were packed in a quartz glass reactor having an internal diameter of 8 mm and the catalyst bed was fixed at its end portions by means of glass wool. A mixed gas of propylene-ammonia-oxygen-nitrogen (1:1.2:1.9:12.7) was passed through the reactor at a rate of 1.2 liters/hour in terms of volume under normal temperature and pressure (N.T.P.) conditions while maintaining the reaction temperature at 460° C. and the reaction pressure at atmospheric pressure. Under the reaction conditions, the time of contact of the mixed gas with the catalyst was 2.2 seconds.

The products of the ammoxidation reaction according to the above-mentioned two processes were analyzed by a gas chromatographic method. The results are shown in Table 1 and 2, together with the composition of a catalyst used. Catalyst 14 was obtained by calcining the dried powder of raw material at 630° C. for 2 hours and the other catalysts were obtained by calcining the dried powder of raw material at 690° C. for 2 hours. In Tables 1 and 2, the total conversion of propylene, the selectivity for acrylonitrile and the yield of acrylonitrile are those obtained by the following formulae.

Total Conversion of Propylene
$$= \frac{\text{weight of carbon of reacted propylene}}{\text{weight of carbon of fed propylene}} \times 100$$

Selectivity for Acrylonitrile
$$= \frac{\text{weight of carbon of formed acrylonitrile}}{\text{weight of carbon of reacted propylene}} \times 100$$

Yield of Acrylonitrile
$$= \frac{\text{weight of carbon of formed acrylonitrile}}{\text{weight of carbon of fed propylene}} \times 100$$

TABLE 1

(Comparison between Fluidized Bed Process and Fixed Bed Process)

| Catalyst | X | Y | Z | a | p | SiO₂ (% by weight) |
|---|---|---|---|---|---|---|
| 2 | 0.50 | 0.60 | 0.3 | K 0.006 | 0.1 | 50 |
| 12 | 0.725 | 0.525 | 0 | K 0.006 | 0.1 | 50 |

| | Fluidized Bed Process | | | Fixed Bed Process | | |
|---|---|---|---|---|---|---|
| | Total Conversion of Propylene (%) | Acrylonitrile Selectivity (%) | Yield (%) | Total Conversion of Propylene (%) | Acrylonitrile Selectivity (%) | Yield (%) |
| Catalyst | | | | | | |
| 2 | 98.8 | 76.9 | 76.0 | 99.0 | 81.4 | 80.6 |
| 12 | 98.7 | 82.0 | 80.9 | 98.8 | 86.3 | 85.3 |

Table 1 shows the comparison of reaction performance between a fluidized bed process and a fixed bed process according to which ammoxidation reactions of propylene were respectively carried out using two catalysts within the scope of the present invention. It will be apparent from Table 1 that the fixed bed process was superior in reaction performance, especially in yield of acrylonitrile, to the fluidized bed process with respect to both of the catalysts used. However, a fluidized bed process is generally adopted in the commercial scale production of acrylonitrile because of easiness of the running operation. Accordingly, the ammoxidation reactions of propylene by the use of the other catalysts were carried out according to a fluidized bed process. The results are shown in Table 2.

TABLE 2

(Fluidized Bed Process)

| | Catalyst | X | Y | Z | a | | p | SiO₂ (% by weight) | Total Conversion of Propylene (%) | Acrylonitrile Selectivity (%) | Yield (%) |
|---|---|---|---|---|---|---|---|---|---|---|---|
| Present Invention | 1 | 0.50 | 0.40 | 0.1 | K | 0.006 | 0.1 | 50 | 98.1 | 78.3 | 76.8 |
| Present Invention | 2 | 0.50 | 0.60 | 0.3 | K | 0.006 | 0.1 | 50 | 98.8 | 76.9 | 76.0 |

TABLE 2-continued
(Fluidized Bed Process)

| | Catalyst | Composition of Catalyst | | | | | SiO₂ (% by weight) | Total Conversion of Propylene (%) | Acrylonitrile Selectivity (%) | Yield (%) |
| | | X | Y | Z | a | p | | | | |
| --- | --- | --- | --- | --- | --- | --- | --- | --- | --- | --- |
| Present Invention | 3 | 0.65 | 0.45 | 0.1 | K | 0.006 0.1 | 50 | 98.5 | 79.2 | 78.0 |
| Present Invention | 4 | 0.65 | 0.50 | 0 | K | 0.006 0.1 | 50 | 98.4 | 81.0 | 79.7 |
| Present Invention | 5 | 0.65 | 0.50 | 0.2 | K | 0.006 0.1 | 50 | 98.8 | 81.5 | 80.5 |
| Present Invention | 6 | 0.65 | 0.50 | 0.2 | K | 0.012 0.1 | 50 | 98.3 | 80.3 | 78.9 |
| Present Invention | 7 | 0.65 | 0.50 | 0.2 | K | 0.018 0.1 | 50 | 97.0 | 79.3 | 76.9 |
| Present Invention | 8*1 | 0.65 | 0.50 | 0.2 | Rb | 0.004 0.1 | 50 | 98.0 | 81.0 | 79.4 |
| Present Invention | 9*2 | 0.65 | 0.50 | 0.2 | K / Rb | 0.003 0.1 / 0.002 | 50 | 98.2 | 80.7 | 79.2 |
| Present Invention | 10*3 | 0.65 | 0.50 | 0.2 | Cs | 0.003 0.1 | 50 | 98.5 | 80.7 | 79.5 |
| Present Invention | 11 | 0.65 | 0.60 | 0.1 | K | 0.006 0.1 | 50 | 98.1 | 78.5 | 77.0 |
| Present Invention | 12 | 0.725 | 0.525 | 0 | K | 0.006 0.1 | 50 | 98.7 | 82.0 | 80.9 |
| Present Invention | 13 | 0.725 | 0.525 | 0.1 | K | 0.006 0.1 | 50 | 98.9 | 81.2 | 80.3 |
| Present Invention | 14*4 | 0.725 | 0.525 | 0.1 | K | 0.006 0.1 | 50 | 98.6 | 77.6 | 76.5 |
| Present Invention | 15 | 0.80 | 0.55 | 0.1 | K | 0.006 0.1 | 50 | 97.2 | 79.5 | 77.3 |
| Comparative | 23 | 0.40 | 0.50 | 0.2 | K | 0.006 0.1 | 50 | 95.2 | 72.8 | 69.3 |
| Comparative | 24 | 0.50 | 0.325 | 0 | K | 0.006 0.1 | 50 | 96.5 | 72.4 | 69.9 |
| Comparative | 25 | 0.50 | 0.70 | 0.3 | K | 0.006 0.1 | 50 | 93.1 | 71.7 | 66.8 |
| Comparative | 26 | 0.65 | 0.35 | 0.1 | K | 0.006 0.1 | 50 | 95.7 | 72.2 | 69.1 |
| Comparative | 27 | 0.65 | 0.40 | 0 | K | 0.006 0.1 | 50 | 96.7 | 75.3 | 72.5 |
| Comparative | 28 | 0.65 | 0.50 | 0 | | 0 0.1 | 50 | 94.1 | 73.6 | 69.3 |
| Comparative | 29 | 0.65 | 0.50 | 0.2 | K | 0.027 0.1 | 50 | 95.2 | 77.3 | 73.6 |
| Comparative | 30 | 0.65 | 0.50 | 0.2 | K | 0.035 0.1 | 50 | 93.8 | 76.5 | 71.8 |
| Comparative | 31 | 0.65 | 0.50 | 0.2 | K | 0.006 0.1 | 80 | 90.5 | 70.8 | 64.1 |
| Comparative | 32 | 0.65 | 0.60 | 0.7 | K | 0.006 0.1 | 50 | 95.4 | 75.8 | 72.3 |
| Comparative | 33 | 0.65 | 0.675 | 0.2 | K | 0.006 0.1 | 50 | 97.5 | 74.3 | 72.4 |
| Comparative | 34 | 0.65 | 0.725 | 0.3 | K | 0.006 0.1 | 50 | 96.3 | 70.8 | 68.2 |
| Comparative | 35 | 0.725 | 0.525 | 0.1 | | 0 0.1 | 50 | 98.4 | 75.2 | 74.0 |
| Comparative | 36 | 0.80 | 0.45 | 0.1 | K | 0.006 0.1 | 50 | 96.8 | 74.3 | 71.9 |
| Comparative | 37 | 0.80 | 0.70 | 0.2 | K | 0.006 0.1 | 50 | 97.3 | 73.7 | 71.7 |
| Comparative | 38 | 0.90 | 0.55 | 0.2 | K | 0.006 0.1 | 50 | 96.4 | 73.2 | 70.6 |

Note
*1 and *2: Rubidium nitrate was used as the source of Rb.
*3: Cesium nitrate was used as the source of Cs.
*4: Calcined at 630° C. for 2 hours.

In Table 2, Catalysts 1 to 15 are those which satisfy all of the requirements with respect to the composition of a catalyst to be used in the process of the present invention, whereas Catalysts 23 to 38 are those which satisfy at least one of the requirements with respect to the composition of a catalyst to be used in the process of the present invention but do not satisfy all of the requirements and, accordingly, are marked as "Comparative".

As apparent from Table 2, when the ammoxidation reaction of propylene was carried out using any of Catalysts 1 to 15 according to the process of the present invention, the yield of acrylonitrile was as high as 76% or more. When Comparative Catalysts 28 and 35 containing no ingredient A were respectively used, the yields of acrylonitrile were 69.3% in the case of Catalysts 28 and 74.0% in the case of Catalyst 35. On the other hand, when Catalysts 4 and 13 containing potassium as the ingredient A (present invention) were respectively used, the yields of acrylonitrile were so remarkably improved as to be as high as 79.7% in the case of Catalyst 4 corresponding to Catalyst 28 and 80.3% in the case of Catalyst 13 corresponding to Catalyst 35.

When Comparative Catalysts 29 and 30 containing so much potassium as to exceed the upper limit of the content of the ingredient A of a catalyst to be used in the process of the present invention were respectively used, the selectivities for acrylonitrile were relatively low and the activities of the catalysts were particularly low. Therefore, the total conversions of propylene were notedly low and, as a result, the yields of acrylonitrile were inevitably low, as compared with those in the case ene and the selectivity for acrylonitrile are shown in FIGURE.

In Table 3, the definitions with respect to the total conversion of propylene, the selectivity for acrylonitrile and the yield of acrylonitrile are the same as described hereinbefore, and the yield of a by-product is that obtained by the following formula.

$$\text{Yield of By-product} = \frac{\text{weight of carbon of by-product}}{\text{weight of carbon of fed propylene}} \times 100$$

TABLE 3

| | | | (Fluidized Bed Process) | | | | | |
|---|---|---|---|---|---|---|---|---|
| | | Time of Contact (second) | Total Conversion of Propylene (%) | Acrylonitrile | | Yield of By-product (%) | | |
| | Catalyst | | | Selectivity (%) | Yield (%) | $CH_3CN$ | HCN | Acrolein | $CO_2 + CO$ |
| Present Invention | 5 | 3.3 | 89.2 | 84.2 | 75.1 | 2.3 | 5.7 | 1.2 | 4.9 |
| Present Invention | 5 | 4.2 | 94.3 | 83.1 | 78.4 | 2.0 | 6.5 | 1.0 | 6.4 |
| Present Invention | 5 | 6.6 | 98.8 | 81.5 | 80.5 | 2.0 | 7.0 | 1.0 | 8.3 |
| Comparative | 28 | 5.2 | 88.5 | 77.0 | 68.1 | 2.9 | 5.1 | 1.5 | 10.9 |
| Comparative | 28 | 6.6 | 94.1 | 73.6 | 69.3 | 3.5 | 6.2 | 1.3 | 13.8 |
| Comparative | 28 | 8.0 | 98.1 | 70.0 | 68.7 | 3.4 | 6.8 | 1.2 | 18.0 | where the corresponding Catalysts 5, 6 and 7 (present invention) were respectively used.

The uses of Comparative Catalysts 23, 24, 25, 26, 27, 33, 34, 36, 37 and 38 fall outside the scope of the present invention because these catalysts do not satisfy the requirement regarding the composition indices X and Y of a catalyst to be used in the process of the present invention. The use of Comparative Catalyst 32 falls outside the scope of the present invention because the composition index Z of the catalyst exceeds the upper limit of the composition index Z of a catalyst to be used in the process of the present invention. When these catalysts were respectively used, the yields of acrylonitrile were low though the catalysts contained potassium as the ingredient A.

The use of Comparative Catalysts 31 falls outside the scope of the present invention because the content of silica as the support exceeds that of a catalyst to be used in the process of the present invention. When Comparative Catalyst 31 was used, the total conversion of propylene was extremely low due to the low activity of the catalyst.

For clarifying the effects of the ingredient A, the ammoxidation reactions were carried out using the above-mentioned Catalyst 5 and Comparative Catalyst 28, respectively, according to substantially the same fluidized bed process as described hereinbefore except that the time of contact of the mixed gas with the catalyst was changed. The results are shown in Table 3 and the relationship between the total conversion of propyl- As apparent from Table 3, when Catalyst 5 (present invention) was used, not only the selectivity for acrylonitrile was high but also the high selectivity for acrylonitrile was maintained even at the increased total conversion of propylene, while, when Comparative Catalyst 28 was used, the selectivity for acrylonitrile was relatively low and showed a tendency to decrease drastically as the total conversion of propylene was increased by prolonging the time of contact of the mixed gas with the catalyst. This fact will be better understood when reference is made to FIGURE. The reason is believed to be that, in the case where Catalyst 28 was used, the acrylonitrile formed underwent secondary decomposition to a considerable extent.

(3) Escaping of Molybdenum

The test for estimation of escaping of molybdenum was conducted as follows. About 10 g of a catalyst on a porcelain dish was weighed accurately and allowed to stand in the presence of air at 750° C. for 100 hours, followed by accurate weighing of the catalyst. Escaping (in terms of percent by weight based on the catalyst) of molybdenum was calculated from the weight decrease of the catalyst. It was confirmed by the elementary analysis of the catalyst conducted after the test that the weight decrease of the catalyst was due to sublimation-escaping of $MoO_3$.

Escaping of molybdenum was examined with respect to catalysts as indicated in Table 4 and the results were as shown in Table 4.

TABLE 4

| | Catalyst | Composition of Catalyst | | | | | | Escaping of Molybdenum (%) |
|---|---|---|---|---|---|---|---|---|
| | | X | Y | Z | a | p | $SiO_2$ (% by weight) | |
| Present Invention | 4 | 0.65 | 0.50 | 0 | K | 0.006 | 0.1 | 50 | 0.85 |
| Present Invention | 5 | 0.65 | 0.50 | 0.2 | K | 0.006 | 0.1 | 50 | 0.40 |
| Present Invention | 16 | 0.65 | 0.60 | 0 | K | 0.006 | 0.1 | 50 | 1.24 |
| Present Invention | 11 | 0.65 | 0.60 | 0.2 | K | 0.006 | 0.1 | 50 | 0.81 |

TABLE 4-continued

| | Catalyst | Composition of Catalyst | | | | | SiO2 (% by weight) | Escaping of Molybdenum (%) |
| | | X | Y | Z | a | p | | |
|---|---|---|---|---|---|---|---|---|
| Present Invention | 17 | 0.65 | 0.60 | 0.4 | K 0.006 | 0.1 | 50 | 0.49 |
| Comparative | 39 | 0.65 | 0.725 | 0 | K 0.006 | 0.1 | 50 | 4.26 |
| Comparative | 34 | 0.65 | 0.725 | 0.3 | K 0.006 | 0.1 | 50 | 2.54 |

As apparent from Table 4, Comparative Catalysts 39 and 34 having a composition index Y exceeding the upper limit defined with respect to the composition index Y of a catalyst to be used in the process of the present invention showed large escaping of molybdenum. Comparative Catalyst 34 showed escaping of molybdenum suppressed to some extent by incorporation of sodium (introduction of Z) as compared with Catalyst 39, but the use of Catalyst 34 gave a low yield of acrylonitrile as apparent from Table 2. In the process of the present invention, however, since the catalysts to be used have a composition index Y in the limited range, they are effectively prevented from escaping of molybdenum incorporated therein. Further, occasionally, by incorporation of sodium (introduction of Z), the preventive effect against escaping of molybdenum can be further enhanced.

(4) Attrition of Catalyst

The attrition resistances of catalysts were measured according to substantially the same test method for an FCC catalyst (catalyst for fluid catalytic cracking process).

About 50 g of a catalyst was weighed accurately and placed in a vertical tube having an internal diameter of 1.5 inches and a height of 30 inches and provided at the bottom with a perforated disc having three orifices whose diameters were each 1/64 inch. Air started to be introduced through the orifices of the perforated disc into the tube at a rate of 15 cubic feet/hour, whereby the catalyst was vigorously fluidized. The attrition degree of the catalyst was evaluated in terms of percentage of the weight of the fine catalyst particles produced by attrition and blown off from the top of the vertical tube during the period of from 5 hours to 20 hours, relative to the initial weight of the catalyst charged.

The attrition degree was examined with respect to the catalysts as indicated in Table 5 and the results were as shown in Table 5.

20, 5, 21 and 22 containing a suitable amount of silica (present invention) underwent attrition to only a small extent. Table 5 also shows a preventive effect of phosphorus incorporation against attrition.

What is claimed is:

1. A process for the preparation of acrylonitrile by the gaseous phase reaction of propylene with ammonia and molecular oxygen in the presence of a catalyst, characterized in that the sole catalyst is:

a catalyst composition represented by the following general formula $$A_a Mo Bi_b Fe_f Na_n P_p O_q$$

wherein

A is at least one element selected from potassium, rubidium and cesium;

a, b, f, n, p and q are numbers respectively representing atomic ratios of A, bismuth, iron, sodium, phosphorus and oxygen relative to one atom of molybdenum, provided that;

a is a number of 0.002 to 0.2;

p is a number of 0 to 0.2;

q is the number of oxygens required to satisfy the valence requirements of the other elements present; and b, f and n are numbers respectively defined by the following formulae $$b = \frac{(1-X)(1-Y)(1-Z)}{Y} + \frac{1}{2}Z + p,$$

$$f = \frac{X(1-Y)(1-Z)}{Y} \text{ and } n = \frac{1}{2}Z$$

wherein

X and Y are respectively numbers falling within the area defined by a quadrilateral formed by lines connecting points (0.45, 0.35), (0.45, 0.65), (0.85, 0.50) and (0.85, 0.65) on an XY diagrammatic system of coordinates; and

TABLE 5

| | Catalyst | Composition of Catalyst | | | | | SiO2 (% by weight) | Attrition Degree (%) |
| | | X | Y | Z | a | p | | |
|---|---|---|---|---|---|---|---|---|
| Present Invention | 18 | 0.65 | 0.50 | 0.20 | K 0.006 | 0.10 | 40 | 1.48 |
| Present Invention | 19 | 0.65 | 0.50 | 0.20 | K 0.006 | 0 | 50 | 1.88 |
| Present Invention | 20 | 0.65 | 0.50 | 0.20 | K 0.006 | 0.05 | 50 | 1.24 |
| Present Invention | 5 | 0.65 | 0.50 | 0.20 | K 0.006 | 0.10 | 50 | 0.50 |
| Present Invention | 21 | 0.65 | 0.50 | 0.20 | K 0.006 | 0.20 | 50 | 0.35 |
| Present Invention | 22 | 0.65 | 0.50 | 0.20 | K 0.006 | 0.10 | 60 | 0.42 |
| Comparative | 40 | 0.65 | 0.50 | 0.20 | K 0.006 | 0.10 | 10 | 8.36 |
| Comparative | 41 | 0.65 | 0.50 | 0.20 | K 0.006 | 0.10 | 20 | 5.28 |

As apparent from Table 5, Comparative Catalysts 40 and 41 containing a small amount of silica underwent attrition to a considerable extent, while Catalysts 18, 19, Z is a number of 0 to 0.6; said catalyst composition being supported on 30 to 70% by weight, based on said catalyst, of silica.

2. A process according to claim 1, wherein the ingredient A is potassium.

3. A process according to claim 1, wherein the index a is in the range of 0.004 to 0.012.

4. A process according to claim 2, wherein the index a is in the range of 0.004 to 0.012.

5. A process according to claim 4, wherein the index p is in the range of 0.05 to 0.15.

6. A process according to claim 1, wherein the index Z is in the range of 0 to 0.45.

7. A process according to claim 1, wherein the index Z is zero and the indices X and Y are respectively numbers falling within the area defined by a quadrilateral formed by lines connecting points (0.45, 0.35), (0.45, 0.55), (0.85, 0.50) and (0.85, 0.55) on an XY diagrammatic system of coordinates.

8. A process according to claim 1, wherein the silica is present in an amount of 40 to 60% by weight based on said catalyst.

* * * * *